(12) United States Patent
Miller et al.

(10) Patent No.: US 6,180,683 B1
(45) Date of Patent: Jan. 30, 2001

(54) SYNERGISTIC MIXTURES OF ALKYLPHENOL-FORMALDEHYDE RESINS WITH OXALKYLATED AMINES AS ASPHALTENE DISPERSANTS

(75) Inventors: Dennis Miller, Kelkheim; Michael Feustel, Köngernheim; Axel Vollmer, Kriftel; Reinhard Vybiral, Burgkirchen; Dieter Hoffmann, Kastl, all of (DE)

(73) Assignee: Clariant GmbH, Frankfurt (DE)

( * ) Notice: Under 35 U.S.C. 154(b), the term of this patent shall be extended for 0 days.

(21) Appl. No.: 09/036,893

(22) Filed: Mar. 9, 1998

(30) Foreign Application Priority Data

Mar. 10, 1997 (DE) .............................................. 197 09 797

(51) Int. Cl.[7] ........................... B01F 17/40; B01F 17/46; C10G 9/16; E21B 43/28
(52) U.S. Cl. ...................... 516/31; 208/39; 208/48 AA; 507/90; 516/916
(58) Field of Search ............................... 516/31, 916, 45; 44/433, 434; 507/90; 208/39, 48 AA; 106/277

(56) References Cited

U.S. PATENT DOCUMENTS

| | | | |
|---|---|---|---|
| Re. 32,174 | * | 6/1986 | LeSuer ................................ 44/433 X |
| 2,753,303 | * | 7/1956 | Barker ................................. 516/31 X |
| 2,760,852 | | 8/1956 | Stevens et al. ......................... 44/440 |
| 3,390,088 | | 6/1968 | Griffing ................................. 508/585 |
| 3,418,249 | * | 12/1968 | Pitchford .......................... 106/277 X |
| 3,466,247 | * | 9/1969 | Ohtsuka et al. ......................... 516/45 |
| 4,209,422 | * | 6/1980 | Zimmerman et al. ............... 44/433 X |
| 4,414,035 | | 11/1983 | Newberry ................................. 134/3 |
| 4,527,996 | * | 7/1985 | Campbell ................................ 44/434 |
| 5,021,498 | | 6/1991 | Stephenson et al. ................. 524/484 |
| 5,034,508 | * | 7/1991 | Nishizaki et al. .................. 516/31 X |
| 5,421,993 | | 6/1995 | Hille et al. .............................. 208/47 |
| 5,494,607 | | 2/1996 | Manek et al. . |

FOREIGN PATENT DOCUMENTS

| | | |
|---|---|---|
| 2029465 | 5/1991 | (CA) . |
| 2075749 | 2/1993 | (CA) . |
| 1284378 | 12/1968 | (DE) . |
| 0 111 983 * | 6/1984 | (EP) ..................................... 208/39 |
| 0579339 | 1/1994 | (EP) . |
| 0584708 | 3/1994 | (EP) . |

OTHER PUBLICATIONS

Chia–Lu Chang et al., Asphaltene Stabilization in Alkyl Solvents Using Oil–Soluble Amphiphiles, SPE Paper No. 25185, pp. 339–349, 1993.

B. Rowan, "The Use of Chemicals in Oilfield Demulsification", Industrial Applications of Surfactants, p. 247.

M.N. Bouts et al., "An Evaluation of New Asphaltene Inhibitors: Laboratory Study and Field Testing", JPT, Sep. 1995, pp. 782–787.

International Search Report.

* cited by examiner

Primary Examiner—Richard D. Lovering
(74) Attorney, Agent, or Firm—Miles B. Dearth; Scott E. Hanf

(57) ABSTRACT

The present invention relates to a synergistic mixture comprising, as asphaltene dispersant, from 5 to 95% by weight of a compound A of the formula I or II defined in the description, and from 5 to 95% by weight of a compound B of the formula (III) defined in the description, the substituents being defined as described in the description.

The mixture is an excellent asphaltene dispersant in crude oils and products derived therefrom.

6 Claims, 2 Drawing Sheets

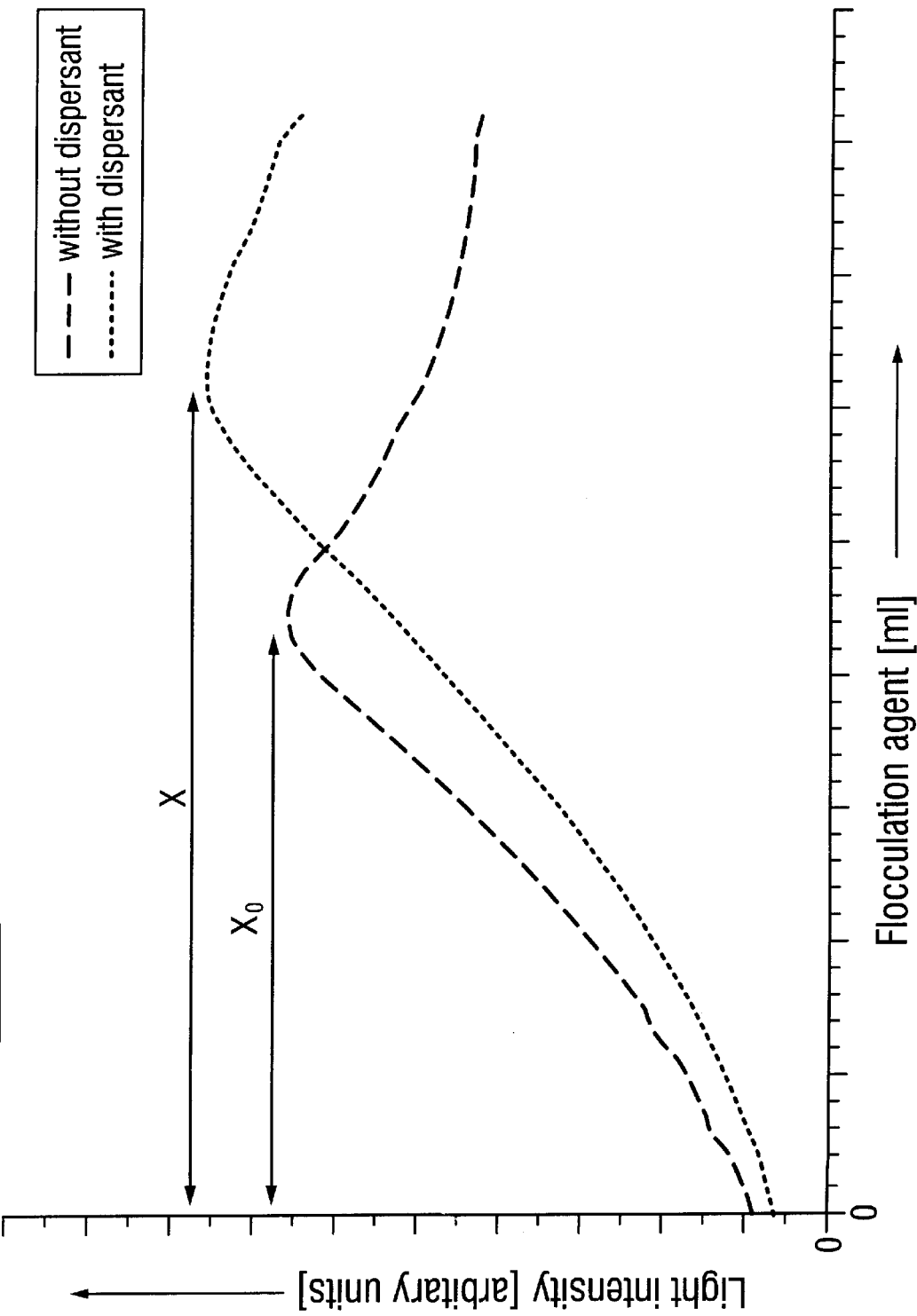

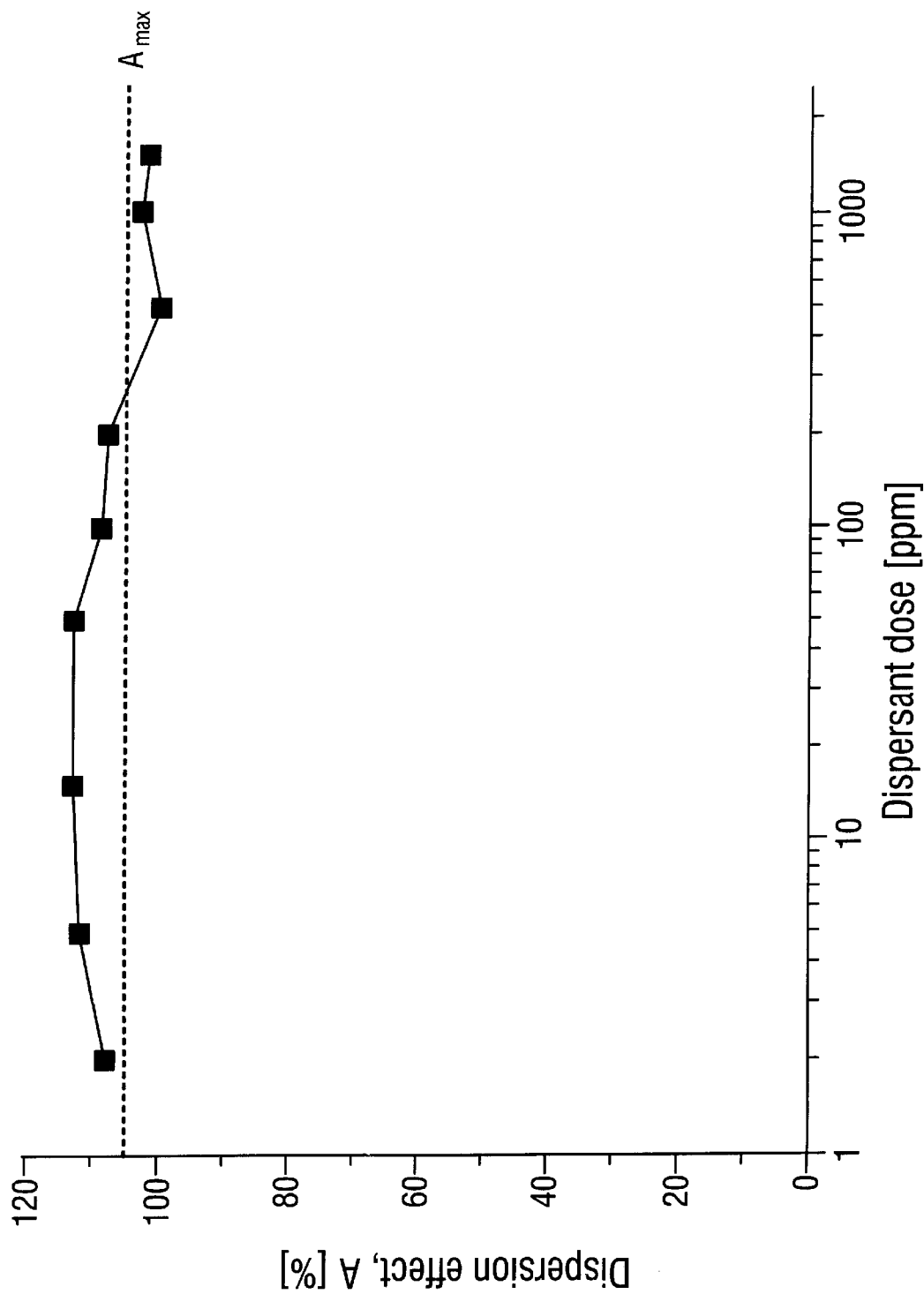

SYNERGISTIC MIXTURES OF ALKYLPHENOL-FORMALDEHYDE RESINS WITH OXALKYLATED AMINES AS ASPHALTENE DISPERSANTS

Asphaltenes are constituents of crude oils. They comprise a large number of structures, in particular high molecular weight fused aromatic components containing heteroatoms. In view of the complexity of their chemistry, asphaltenes are described as the oil fraction which is soluble in benzene, but not in n-pentane.

In crude oil, asphaltenes are usually in the form of a colloidal dispersion. This is stabilized by oil resins.

Asphaltenes can precipitate out during the production, refining, transportation and storage of crude oil and products derived therefrom, such as, for example, heavy heating oil or marine oil. Common causes of this precipitation are a reduction in the temperature or a change in the composition (for example evaporation of readily volatile constituents). Asphaltenes can also precipitate out on flowing through porous media. Flooding with $CO_2$ during the extraction process can make asphaltenes flocculate or precipitate out.

Some oils comprise hydrocarbon waxes which precipitate out at low temperatures. Interactions between the wax precipitates and asphaltenes can increase the total amount of substance precipitated out or the rate of formation thereof.

Asphaltenes which have precipitated out cause problems during the production and processing of crude oils. Asphaltenes are precipitated in valves, pipes and conveying devices. On hot surfaces, such as, for example, heat exchangers, carbonization of these precipitates can make their removal very difficult. The precipitates reduce the efficiency of plants and in the worst case can lead to complete blockage and to a stop in production, which results in high costs.

Heavy oils, which are often used for powering ships, comprise considerable amounts of asphaltenes. The precipitating out of asphaltenes can lead both to poor combustion and to difficulties in the handling and storage of the fuel.

Bitumen, heavy oils and residues are sometimes diluted with solvents to reduce the viscosity for transportation. If asphaltenes precipitate out here, problems arise in handling.

The precipitating out of asphaltenes can be prevented or reduced by small amounts of dispersants. These substances show one or more of the following effects:
a) the amount of precipitate is reduced;
b) the precipitate forms more slowly;
c) the precipitate is more finely divided; and
d) the tendency of the precipitate to be deposited on surfaces is reduced.

If precipitates of asphaltenes have already formed, they can be removed by using solvents. The addition of a dispersant can improve the effectiveness of these solvents.

A large number of asphaltene dispersants are already known. CA 2, 029, 465 and CA 2, 075, 749 describe alkylphenol-formaldehyde resins in combination with hydrophilic-lipophilic vinyl polymers. The asphaltene-dispersing properties of dodecylbenzenesulfonic acid have been described in U.S. Pat. No. 4,414,035, and also by D. -L. Chang and H. S. Fogler (SPE paper No. 25185, 1993) and by M. N. Bouts et al. (J. Pet. Technol. 47, 782–7, 1995).

The preparation of oxalkylated amines and their use as corrosion inhibitors, demulsifiers and paraffin dispersants is described in U.S. Pat. No. 5,421,993. Alkylphenol-formaldehyde resins can be prepared by acidic or basic catalysis. Compounds prepared by acidic catalysis are predominantly linear (cf. formula I), whilst compounds prepared by basic catalysis have a high content of cyclic material, as in Formula II (see B. Rowan in D. Karsa (editor) "Industrial application of surfactants III", p. 247).

The dispersants known to date are able to solve only partially the problems caused by the precipitating out of asphaltenes. Since oils vary in their composition, individual dispersants can only be effective in a limited range. Even small changes in the composition of the oil sometimes have a great effect on the dispersing properties of asphaltenes. In some cases, therefore, the known dispersants are unsatisfactory and additional types are required.

The object was, therefore, to provide novel asphaltene dispersants which do not have the disadvantages described of the dispersants known to date.

It has now been found that combinations of alkylphenol resins and oxalkylated amines have a stronger asphaltene-dispersing effect than the individual substances. This synergy is surprising since a reduction in the effectiveness would be expected in this type of combination of acidic and basic compounds as a consequence of partial neutralization.

The invention therefore relates to a synergistic mixture comprising from 5 to 95% by weight, preferably from 20 to 80% by weight, of a compound A of the formula (I) or (II)

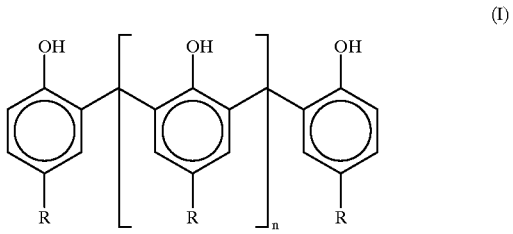

(I)

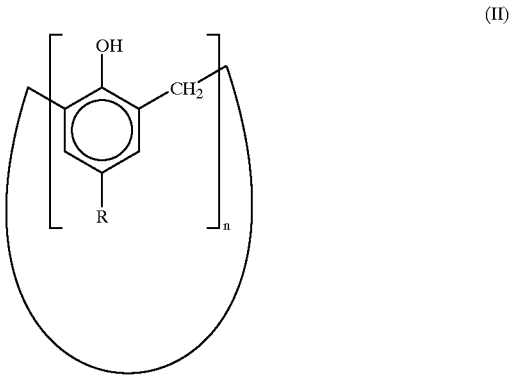

(II)

where
n is from 2 to 12, preferably from 5 to 9, and
R is $C_3$–$C_{24}$-alkyl, preferably $C_4$–$C_{12}$-alkyl, in particular isononyl, isobutyl or amyl, $C_6$–$C_{12}$-aryl or -hydroxyaryl or $C_7$–$C_{12}$-aralkyl
and
from 5 to 95% by weight, preferably from 20 to 80% by weight, of a compound B of the formula (III)

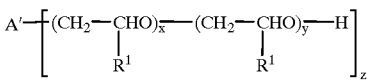

(III)

in which
x and y, independently of one another, are a number from 0 to 120, preferably from 5 to 80, the sum x+y being at least 5, z is 1, 2, 3 or 4, preferably 4,
R$^1$ is hydrogen or methyl,
A' is a radical of the formulae (IV) to (VII), preferably (VII)

(IV)

z = 2

(V)

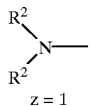

z = 1

(VI)

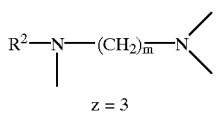

z = 3

(VII)

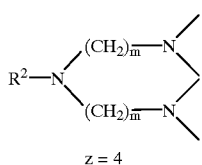

z = 4 where
R$^2$ is a C$_6$–C$_{22}$-alkyl radical, preferably a C$_6$–C$_{18}$-alkyl radical, and
m is 2, 3 or 4; preferably 2 or 3.

Mixtures which are particularly suitable are those in which component A is an isononylphenol-formaldehyde resin or an isononyl/isobutylphenol-formaldehyde resin and component B is an oxalkylated star-shaped amine of the formula (III), in which
A' is a radical of the formula (VII),
z is 4,
R$^2$ is C$_{12}$–C$_{14}$-alkyl,
m is 3 and
x and y, independently of one another, are a number from 0 to 60, the sum x+y being at least 5.

The invention further relates to crude oils and products derived therefrom comprising, as asphaltene dispersant, a synergistic combination of alkylphenol resins with oxalkylated amines, as described above.

Products derived from crude oil are, for example, heavy heating oil, marine oil or bitumen.

The oxalkylated fatty amines and fatty amine derivatives of the formula (III) are prepared by customary oxalkylation processes, which involve reacting an amine of the formula (IV) to (VII) with ethylene oxide alone (R$^1$ is H and the polyoxyalkylene radical consists of ethylene oxide units) or with propylene oxide alone (R$^1$ is CH$_3$ and the polyoxyalkylene radical consists of propylene oxide units) or with ethylene oxide and propylene oxide simultaneously or successively (R$^1$ is H and CH$_3$ and the polyoxalkylene radical consists of ethylene oxide and propylene oxide units which are randomly distributed or in block form). The reaction is generally carried out at a temperature of from 100 to 180° C., in the absence or presence of an alkaline or acidic oxalkylation catalyst, with exclusion of air.

The amine compounds of the formula (III) and their preparation are described in detail in U.S. Pat. No. 5,421,993, which was cited at the beginning and which is expressly incorporated herein by way of reference. They are obtained by oxalkylation of amines of the formulae (IV) to (VII) defined above, firstly using ethylene oxide and then using propylene oxide, with the addition of bases, such as alkali metal hydroxides. The reaction is carried out in stages at a temperature of, preferably, from 100 to 160° C. The amount of catalyst/base used is generally from 0.5 to 3.0% by weight, based on the starting amine used. The molar amount of ethylene oxide and propylene oxide per mole of starting amine corresponds to the values specified for x and y. Reference is made to the cited U.S. Pat. No. 5,421,993 for details.

The compound of the formula (I) or (II) can be neutralized completely or partially using NaOH, KOH, NH$_3$ or amine. Both the acidic and the neutralized forms are effective.

For some oils, an acidic asphaltene dispersant is advantageous. This can be achieved by adding acids, such as, for example, acetic acid. Particularly suitable acids are organic acids having surfactant properties, such as mono- or dialkylbenzenesulfonic acids, petroleum sulfonic acids and alkanesulfonic acids.

The synergistic mixture according to the invention is used in a concentration of from 0.5 to 10,000 ppm, preferably from 2 to 2000 ppm.

To achieve easier dosing, this mixture can be formulated as a solution in an oil-miscible solvent, such as, for example, aromatic hydrocarbons or mixtures of hydrocarbons and an aliphatic alcohol.

Since the synergistic mixture according to the invention is based on a combination of substances, it may be less sensitive to a change in the composition of the oil; this improves its reliability.

EXAMPLES

Test substances

Component A:

A I: Isononylphenol-formaldehyde resin (acid-catalyzed), neutralized with KOH

A II: Isononylphenol-formaldehyde resin (acid-catalyzed), unneutralized

A III: Alkylphenol-formaldehyde resin (acid-catalyzed), neutralized with KOH, alkyl chain=1:1 isononyl/isobutyl mixture The mean value for n, calculated from the molecular weight, was about 8.6.

Component B:

B I: Oxalkylated star-shaped amine

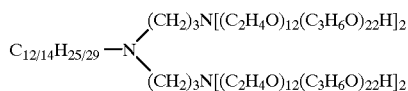

B II: Oxalkylated star-shaped amine

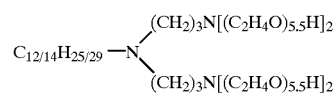

B III: Oxalkylated star-shaped amine

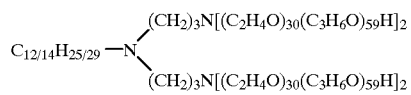

The formaldehyde resin A I was prepared by reacting p-nonylphenol with an equimolar amount of a 35% by weight strength formalin solution in the presence of catalytic amounts of alkylbenzenesulfonic acid, removing the water from the reaction mixture azeotropically using a mixture of higher boiling aromatic hydrocarbons (boiling range 185–215° C.) and neutralizing the mixture with potassium hydroxide. The red-brown resin was diluted in ®Solvent Naphtha to a solids content of 50%. The molecular weight, determined by gel permeation chromatography (calibration using a polystyrene standard), is 2000 g/mol.

Testing the effectiveness of asphaltene dispersants

Flocculation test: method

The dispersing, the precipitating out of asphaltenes depends on the nature of the hydrocarbon medium. Asphaltenes are soluble in aromatic, but not in aliphatic hydrocarbons. Dispersants can thus be tested by dissolving the oil or extracted asphaltenes in an aromatic solvent or cycloalkane and then adding an aliphatic hydrocarbon until flocculation and/or a precipitate appears. This flocculation can be observed using light transmission. Upon adding the aliphatic hydrocarbon, the transmission initially increases as a result of the dilution effect. When the asphaltenes begin to flocculate, the turbidity then reduces the light transmission. As FIG. 1 shows, a maximum light transmission is observed; this is used as the start of flocculation. This test has been described in a variety of scientific publications, e.g. D. Kessel, H. J. Neumann and I Rahimian, "Asphaltics in Crude Oil-water Emulsions", Proc. 1st World Congress on Emulsions, Paris, 1993, Paper 1-22-071.

The more aliphatic precipitant which can be added before the onset of flocculation, the better the dispersant. The amount of precipitant required to dissolve the flocculation can be used to compare dispersants. To assess the relative effectiveness P of dispersants, the following formula was used:

$$P=100(X/X_0-1)$$

X is the amount of precipitant which, in the presence of a dispersant, is required to dissolve the flocculation. $X_0$ is the amount of precipitant which dissolves the flocculation if no dispersant is present.

Principle of the dispersing test

This test is also based on the fact that asphaltenes are soluble in aromatic, but not in aliphatic hydrocarbons. Dispersants can thus be tested by dissolving the oil or extracted asphaltenes in an aromatic solvent and then adding an aliphatic hydrocarbon in order to produce a precipitate. Since asphaltenes are dark in color, the extent of the precipitate can be determined by a calorimetric measurement of the supernatant liquid. The darker the supernatant liquid, the more asphaltenes remain dispersed, i.e. the better the dispersant. This test is described in CA 2, 029, 465. In our version of the test, the precipitating medium is chosen such that the asphaltenes precipitate out for the most part, but not completely.

Dispersing test procedure a) A 25% strength oil solution in toluene is filtered in order to remove impurities;
b) 9.5 ml of heptane, as a precipitant for asphaltenes, and 0.5 ml of toluene/dispersant mixture (25:1) are introduced into a graduated glass tube which holds a good 10 ml, and are shaken vigorously. This corresponds to a dispersant concentration of 2000 ppm. The amount of dispersant can be varied if required. Pure toluene is used for the blank samples;
c) 0.1 ml of the filtered oil solution is then added to the glass tube and the mixture is likewise shaken vigorously;
d) the entire system is left to stand for 2 hours without vibration. The asphaltenes which have precipitated out should be able to accumulate on the bottom of the tube;
e) after the end of this period, the sediment volume is estimated with the aid of the graduation, the appearance of the entire sample is recorded and then 1 ml of the supernatant phase is carefully removed using a pipette;
f) the quantity aspirated out is dissolved in 5 ml of a 99:1 toluene/triethanolamine mixture and measured photometrically at 600 nm.

Evaluation of the dispersing test

The following expression is used as a relative measure of the dispersing action $$A=100(D-D_o)/D_o,$$

in which D and $D_0$ are the optical densities of the measurement solution and blank sample respectively. The maximum value of A which can be achieved, $A_{max}$, corresponds to complete dispersion of the asphaltenes. It can be estimated by carrying out a test without a dispersant and with toluene instead of heptane—the asphaltenes remain completely dispersed as a result.

The volume of the sediment provides further information on the effectiveness of the dispersant. The smaller the amount of sediment, the better the substance is dispersed.

Example 1

Substances A I, B I and a mixture of A I and B I were tested on a light crude oil from the North Sea using the flocculation test. A 1:1 mixture of oil and cyclohexane was prepared and n-pentane was added in stages. The dispersant dose was 2000 ppm.

The results in Table 1 show that the mixture of I and II has a better action than the individual components.

TABLE 1

| Dispersant | Rel. Dispersion effect P[%] | |
|---|---|---|
| 1:1 Mixture of A I and B I | 14.5 | Mixture according to the invention |
| A I | 3.9 | Comparative experiment |
| B I | 1.2 | Comparative experiment |

Example 2

A mixture according to the invention was tested on an asphaltene-rich oil from Venezuela using the dispersing test. The dispersant comprised a mixture of 7 parts of substance A I and 3 parts of substance B II. The dispersion effect as a function of the dose is shown in FIG. 2. This mixture has a good dispersion effect even at a dose of 2 ppm. Based on the amount of oil, this dose corresponds to 500 ppm. In practice, the required dose is dependent both on the type of oil and also on the technical requirements.

Examples 3–7

Mixtures according to the invention were tested on the asphaltene-rich oil from Venezuela mentioned in Example 2 using the dispersing test. The dose was 2000 ppm.

| Example No. | Component A | Component B | Dispersion effect A[%] | Sediment volume ml |
|---|---|---|---|---|
| 3 | A I 20% | B I 80% | 121 | 0 |
| 4 | A II 50% | B I 50% | 123 | 0 |
| 5 | A II 50% | B I 50% | 115 | 0 |
| 6 | A I 50% | B II 50% | 125 | trace |
| 7 | A I 50% | B III 50% | 121 | 0 |
| Blank | — | — | 0 | 0.45 |

In this test series the maximum dispersion effect $A_{max}$ was about 120%.

What is claimed is:

1. A synergistic mixture comprising, as asphaltene dispersant, from 20 to 80% by weight of a compound A of the formula (I) or (II)

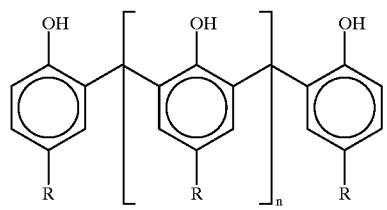
(I)

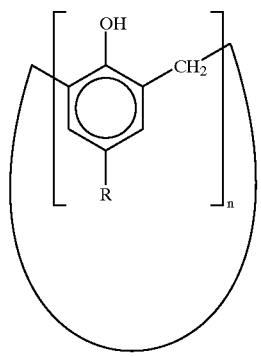
(II)

where
n is from 5 to 9 and
R is $C_4$–$C_{12}$-alkyl, and from 20 to 80% by weight of a compound B of the formula (III)

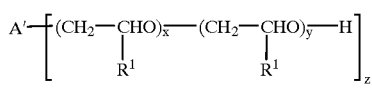
(III)

in which
$R^1$ is hydrogen or methyl
z is 4,
x and y, independently of one another, are a number from 5 to 80,
A' is a radical of the formula (VII),

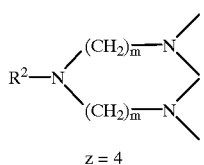
(VII)

z = 4 where
$R^2$ is a $C_6$–$C_{18}$-alkyl radical and
m is 2 or 3.

2. The synergistic mixture as claimed in claim 1, wherein component A is isononylphenol-formaldehyde resin or isononyl/isobutylphenol-formaldehyde resin and component B is an oxalkylated star-shaped amine of the formula (III) in which
A' is a radical of the formula (VII),
z is 4,
$R^2$ is $C_{12}$–$C_{14}$-alkyl,
m is 3 and
x and y, independently of one another, are a number from 5 to 60.

3. A crude oil or product derived therefrom comprising, as asphaltene dispersant, a synergistic mixture as claimed in claim 1.

4. A process for dispersing asphaltenes in crude oils and products derived therefrom, which comprises adding, as dispersant, a synergistic mixture as claimed in claim 1 in an amount of from 0.5 to 10,000 ppm.

5. The process as claimed in claim 4, which comprises additionally using mono- or dialkylbenzenesulfonic acids, petroleum sulfonic acids, alkanesulfonic acids or any desired mixtures thereof.

6. The process of claim 4 wherein said amount of said synergistic mixture is from 2 to 2000 ppm.

* * * * *